United States Patent [19]

Flanigen et al.

[11] Patent Number: 4,686,093

[45] Date of Patent: Aug. 11, 1987

[54] MOLECULAR SIEVE COMPOSITIONS WITH ALUMINUM, PHOSPHORUS AND AT LEAST TWO OTHER ELEMENTS

[75] Inventors: Edith M. Flanigen, White Plains; Brent M. T. Lok, New City; Robert L. Patton, Katonah; Stephen T. Wilson, Shrub Oak, all of N.Y.

[73] Assignee: Union Carbide Corporation, Danbury, Conn.

[21] Appl. No.: 600,171

[22] Filed: Apr. 13, 1984

[51] Int. Cl.$^4$ .................. C01B 25/00; B01J 27/18; B01J 27/188; B01J 27/198

[52] U.S. Cl. .................. 423/306; 502/208; 502/209; 502/210

[58] Field of Search .................. 423/306, 326–333; 502/162, 164, 208, 213, 214, 202, 204, 209, 208, 214

[56] References Cited

U.S. PATENT DOCUMENTS

| | | | |
|---|---|---|---|
| 4,310,440 | 1/1982 | Wilson et al. | 423/305 |
| 4,440,871 | 4/1984 | Lok et al. | 502/214 |
| 4,486,397 | 12/1984 | Eshraghi et al. | 423/306 |
| 4,500,651 | 2/1985 | Lok et al. | 502/208 |
| 4,567,029 | 1/1986 | Wilson et al. | 502/208 |

FOREIGN PATENT DOCUMENTS

| | | |
|---|---|---|
| 0054364 | 6/1982 | European Pat. Off. |
| 0055046 | 6/1982 | European Pat. Off. |
| 0055529 | 7/1982 | European Pat. Off. |
| 0059059 | 9/1982 | European Pat. Off. |

*Primary Examiner*—William R. Dixon, Jr.
*Assistant Examiner*—R. Bruce Breneman
*Attorney, Agent, or Firm*—Vincent J. Vasta, Jr.

[57] ABSTRACT

Crystalline molecular sieves having three-dimensional microporous framework structure of $MO_2$, $AlO_2$, and $PO_2$ tetrahedral oxide units are disclosed. These molecular sieves have an empirical chemical composition on an anhydrous basis are expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least two elements capable of forming framework tetrahedral oxides and selected from the group consisting of arsenic, beryllium, boron, chromium, gallium, germanium, lithium and vanadium; and "x", "y" and 37 z" represent the mole fractions of "M", aluminum and phosphorus, respectively, present as tetrahedral oxides. Their use as adsorbents, catalysts, etc. is disclosed.

45 Claims, 3 Drawing Figures

MOLECULAR SIEVE COMPOSITIONS WITH ALUMINUM, PHOSPHORUS AND AT LEAST TWO OTHER ELEMENTS

FIELD OF THE INVENTION

The instant invention relates to a novel class of crystalline microporous molecular sieves, and to the method of their preparation. The invention relates to novel molecular seives having at least four elements, as hereinafter defined, present as framework as tetrahedral oxide units. These compositions may be prepared hydrothermally from gels containing reactive compounds of aluminum and phosphorus and at least two elements, as hereinafter set forth, capable of forming a framework tetrahedral oxide, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain only $AlO_2$ and $SiO_2$ tetrahedra as essential framework constituents, but which exhibit the ion-exchange and/or adsorption characteristics of the zeolites are also known. Metal organosilicates which are said to possess ion-exchange properties, have uniform pores and be capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, now U.S. Pat. No. 4,440,871 there is described a novel class of silicon-substituted aluminophosphates which are both microporous and crystalline. The materials have a three dimensional crystal framework of $PO_2{}^+$, $AlO_2{}^-$ and $SiO_2$ tetrahedral units and, exclusive of any alkali metal or calcium which may optionally be present, an as-synthesized empirical chemical composition on an anhydrous basis of:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983 now U.S. Pat. No. 4,500,651 there is described a novel class of titanium-containing molecular sieves whose chemical composition in the as-synthesized and anhydrous form is represented by the unit empirical formula:

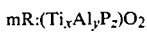

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$; and has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed July 15, 1983 now U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

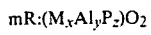

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y" and "z" represent the mole fraction of the metal "M", aluminum and phosphorus, respectively, present as tetrahedral oxides.

In copending and commonly assigned application Ser. No. 514,335, filed July 15, 1983 now U.S. Pat. No. 4,554,143, there is described a novel class of crystalline ferroaluminophosphates having a three-dimensional microporous framework structure of $FeO_2$, $AlO_2$ and $PO_2$ tetrahedral units and having an empirical chemical composition on a anhydrous basis expressed by the formula

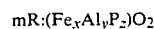

$$mR:(Fe_xAl_yP_z)O_2$$

wherein "R" represents at least one organic templating agent present in the intracrystalline pore system; "m" represents the moles of "R" present per mole of (Fe$_x$Al$_y$P$_z$)O$_2$ and has a value of from zero to 0.3; "x", "y" and "z" represent the mole fraction of the iron, aluminum and phosphorus, respectively, present as tetrahedral oxides.

The instant invention relates to new molecular sieve compositions comprising at least two elements, as hereinafter discussed, capable of forming a framework tetrahedral units with AlO$_2^-$ and PO$_2^+$ tetrahedral units.

SUMMARY OF THE INVENTION

Figure 1:
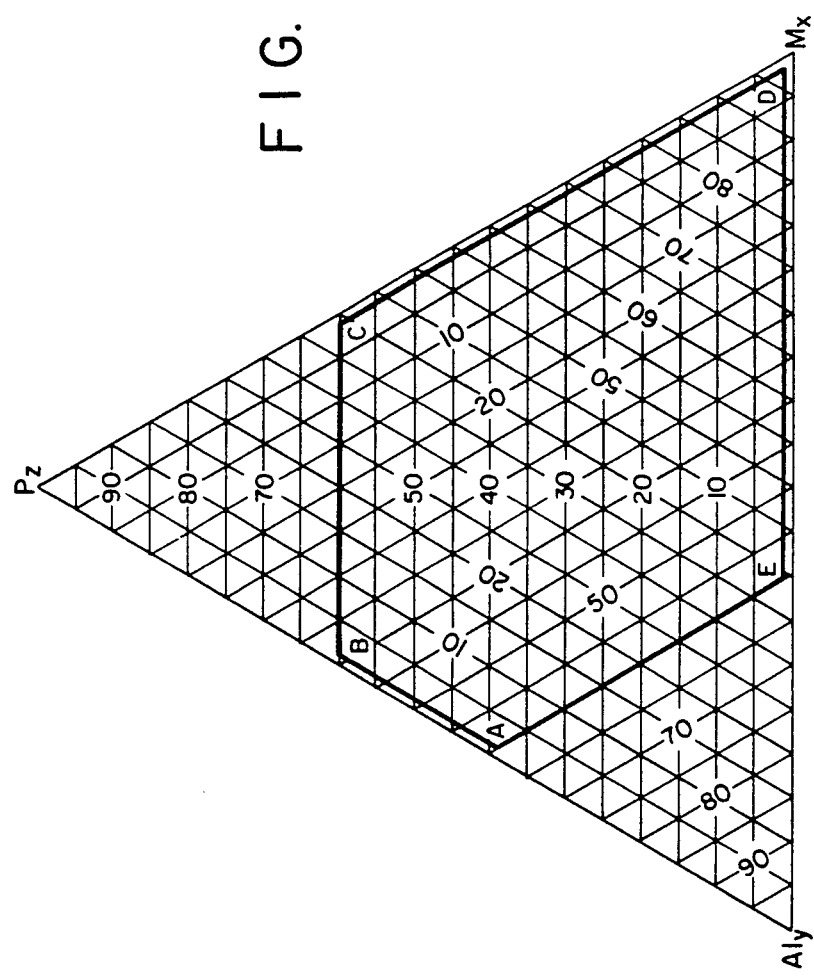
FIG. 1 is a ternary diagram wherein parameters relating to the instant compositions are set forth as mole fractions.

The instant invention relates to a new class of crystalline molecular sieves in which at least two elements in addition to aluminum and phosphorus, as hereinafter defined, capable of forming a three-dimensional microporous framework of framework tetrahedral oxides to form a framework structure of AlO$_2^-$, PO$_2^+$ and MO$_2^n$ tetrahedral units wherein "M" represents at least two different elements present as tetrahedral units with charge "n" where "n" may be $-3$, $-2$, $-1$, 0 or $+1$.

These new molecular sieves exhibit ion-exchange, adsorption and catalytic properties and, accordingly, find wide use as adsorbents and catalysts. The members of this novel class of compositions have crystal framework structures of AlO$_2^-$, PO$_2^+$ and tetrahedral units and have an empirical chemical composition on an anhydrous basis expressed by the formula:

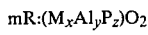

wherein "R" represents at least one organic templating agent present in the intracrystalline pore system; "m" represents the molar amount of "R" present per mole of (M$_x$Al$_y$P$_z$)O$_2$ and has a value of zero to about 0.3; "M" represents at least two elements capable of forming framework tetrahedral oxides and "x", "y" and "z" represent the mole fraction of "M", aluminum and phosphorus, respectively, present an tetrahedral oxides. "M" is at least two different elements such that the molecular sieves contain at least two framework tetrahedral oxides units in addition to AlO$_2^-$ and PO$_2^+$, wherein "M" is at least two elements selected from the group consisting of arsenic, beryllium, boron, chromium, gallium, germanium, lithium and vanadium.

The molecular sieves of the instant invention will be generally referred to herein by the acronym "FCAPO" to designate elements "M" in a framework of AlO$_2^-$, PO$_2^+$ and MO$_2^n$ tetrahedral oxide units. The acronym "FCAPO" denotes "Framework Constituents" of elements "M" in a framework of aluminum and phosphorus where such are all present as framework tetrahedral oxides. Actual class members will be identified by replacing the "FC" of the acronym with the elements present as MO$_2^n$ tetrahedral units. For example, "GeBeAPO" designates a molecular sieve comprised of AlO$_2^-$, PO$_2^+$, GeO$_2$ and BeO$_2^{-2}$ tetrahedral units. To identify various structural species which make up each of the subgeneric classes, each species is assigned a number and is identified as "FCAPO-i" wherein "i" is an integer. The given species designation is not intended to denote a similarity in structure to any other species denominated by a similar identification system.

DETAILED DESCRIPTION OF THE INVENTION

The instant invention relates to a new class of crystalline molecular sieves in which at least two elements capable of forming framework tetrahedral oxides are provided to form a three-dimensional microporous framework structures of AlO$_2^-$, PO$_2^+$ and MO$_2^n$ tetrahedra wherein "M" represents at least two elements capable of forming tetrahedral units "M$_1$O$_2^n$" and "M$_2$O$_2^n$", etc., where "M$_1$" and "M$_2$" are two different elements and where "n" is $-3$, $-2$, $-1$, 0 or $+1$. These new molecular sieves exhibit ion-exchange, adsorption and catalytic properties and, accordingly, find wide use as adsorbents and catalysts.

The FCAPO compositions are formed by forming a framework tetrahedral unit MO$_2^n$ in the presence of AlO$_2^-$ and PO$_2^+$ tetrahedral units where "M" is at least two elements selected from the group consisting of arsenic, beryllium, boron, chromium, gallium, germanium, lithium and vanadium.

The relative amounts of elements "M", aluminum and phosphorus are expressed by the empirical chemical formula (anhydrous):

where "x", "y" and "z" represent the mole fractions of said "M", aluminum and phosphorus. The individual mole fractions of each "M" (M$_1$, M$_2$, M$_3$, etc.) may be represented by "x$_1$", "x$_2$", "x$_3$", etc. wherein "x$_1$", "x$_2$", and "x$_3$" represent the individual mole fractions of elements M$_1$, M$_2$, M$_3$, and etc. for "M" as above defined. The values of "x$_1$", "x$_2$", "x$_3$", etc. are as defined for "x" hereinbefore where "x"=x$_1$+x$_2$+x$_3$, etc., and where x$_1$, xhd 2, x$_3$, etc are each at least 0.01.

The molecular sieves of the instant invention comprise a framework structure of MO$_2^n$, AlO$_2^-$ and PO$_2^+$ tetrahedral units where "n" is $-3$, $-2$, $-1$, 0 or $+1$ and having an empirical chemical composition on an anhydrous basis expressed by the formula:

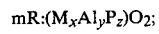

wherein "R" represents at least one organic templating agent present in the intracrystalline pore system; "m" represents the molar amount of "R" present per mole of (M$_x$Al$_y$P$_z$)O$_2$ and has a value of zero to about 0.3; "M" represents at least two different elements capable of forming framework tetrahedral oxides and is at least two elements selected from the class consisting of arsenic, beryllium, boron, chromium, gallium, germanium, lithium and vanadium; and "x", "y" and "z" represent the mole fractions of "M", aluminum and phosphorus, respectively, present as tetrahedral oxides. The mole fractions "x", "y" and "z" are generally defined as being within the pentagonal compositional area defined by points A, B, C, D and E of the ternary diagram of FIG. 1. Points A, B, C, D and E have the following values for "x", "y" and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

Figure 2:
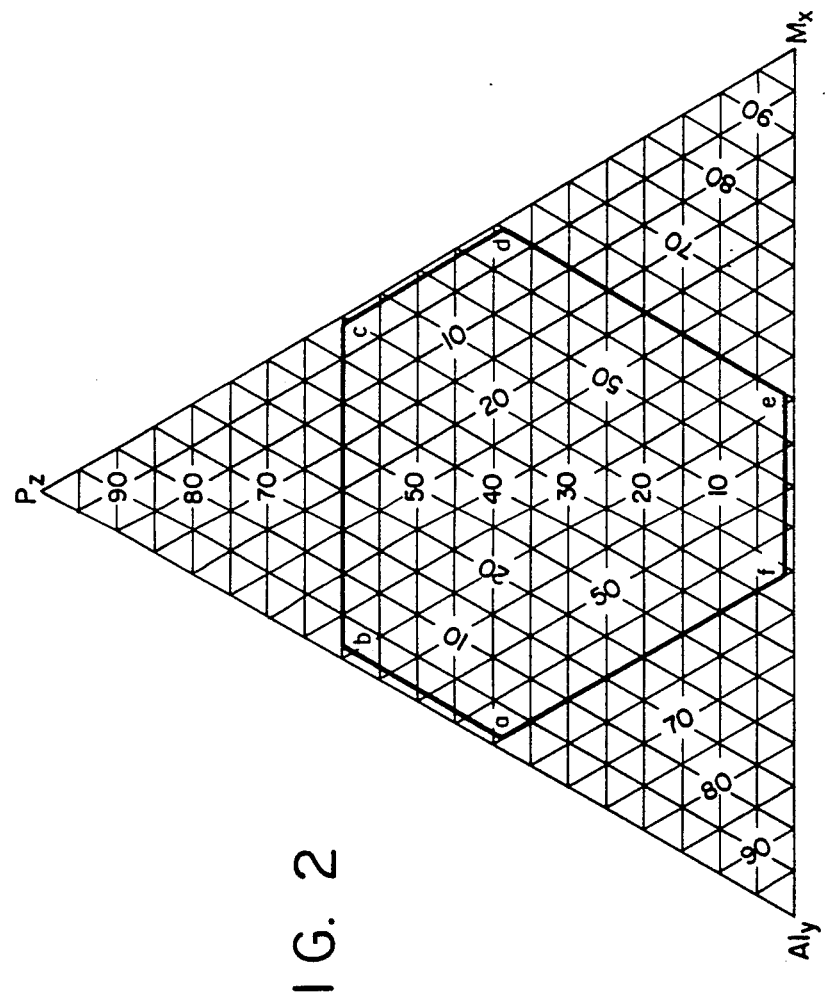
FIG. 2 is a ternary diagram wherein parameters relating to preferred compositions are set forth as mole fractions.

In a preferred subclass of the FCAPO molecular sieves the values of "x", "y" and "z" in the above formula are within the hexagonal compositional area defined by points a, b, c, d, e and f of the ternary diagram which is FIG. 2 of the drawings, said points a, b, c, d, e and f representing the following values for "x", "y" and "z":

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

The FCAPOs of this invention are useful as adsorbents, catalysts, ion-exchangers, and the like in much the same fashion as aluminosilicates have been employed heretofore, although their chemical and physical properties are not necessarily similar to those observed for aluminosilicates.

FCAPO compositions are generally synthesized by hydrothermal crystallization from a reaction mixture containing active sources of elements "M", aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the FCAPO product are obtained, usually a period of from several hours to several weeks. Typical crystallization times are from about 2 hours to about 30 days with from about 4 hours to about 20 days being generally employed to obtain FCAPO products. The product is recovered by any convenient method such as centrifugation or filtration.

In synthesizing the FCAPO compositions of the instant invention, it is preferred to employ a reaction mixture composition expressed in terms of the molar ratios as follows:

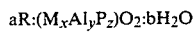

aR:(M$_x$Al$_y$P$_z$)O$_2$:bH$_2$O wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; "M" represents at least two elements capable of forming tetrahedral oxide framework units MO$_2^n$, with AlO$_2^-$ and PO$_2^+$ tetrahedral units where "M" is at least two elements selected from the group consisting of arsenic, beryllium, boron, chromium, gallium, germanium, lithium and vanadium; "n" has a value of $-3$, $-2$, $-1$, 0 or $+1$; and "x", "y" and "z" represent the mole fractions of "M", aluminum and phosphorus, respectively, and "y" and "z" has a value of at least 0.01 and "x" has a value of at least 0.02. The value of "x" is dependent on the number of elements "M" present in the final FCAPO and is 0.01 times the number of elements present in addition to aluminum and phosphorus and thus can range from at least 0.02 to at least 0.08 where from 2 to 8 elements may be present in addition to aluminum and phosphorus. Of course, the aforementioned amounts are minimum amounts and larger effective amounts may be employed.

Figure 3:
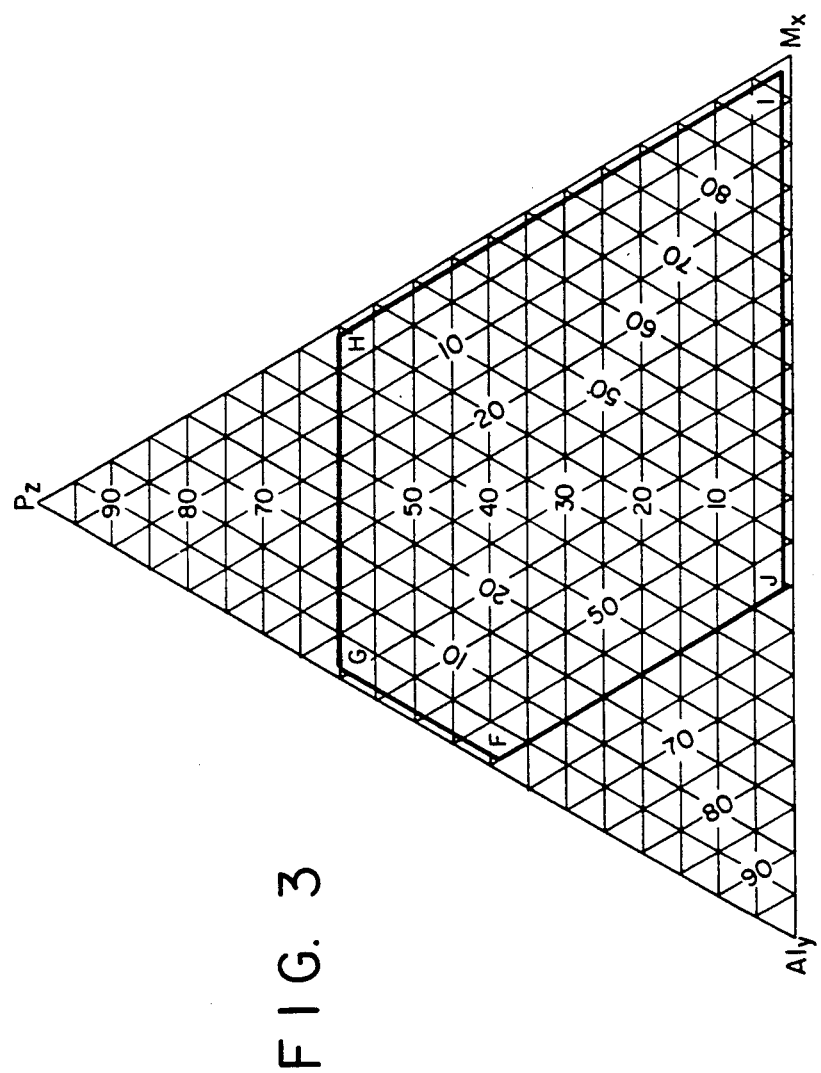
FIG. 3 is a ternary diagram wherein parameters relating to the reaction mixtures employed in the preparation of the compositions of this invention are set forth as mole fractions.

The mole fractions "x", "y" and "z" in the reaction mixture are preferably within the pentagonal compositional area defined by points F, G, H, I and J which is shown in FIG. 3 of the drawings, where points F, G, H, I and J have the following values for "x", "y" and "z":

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to the total of x+y+z=1.00 mole, whereas in the examples the reaction mixtures are expressed in terms of the molar oxide ratios and may be normalized to 1.00 mole of P$_2$O$_5$. This latter form is readily converted to the former by routine calculations by dividing the total number of moles of M, aluminum and phosphorus into the moles of each of the elements "M", aluminum and phosphorus. The moles of template and water are similarly normalized by dividing by the total moles of M, aluminum and phosphorus.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds, and quaternary ammonium compounds, the latter two being represented generally by the formula R$_4$X$^+$, where "X" is nitrogen or phosphorus and wherein each R is an alkyl or aryl group containing from 1 to 8 carbon atoms. Polymeric quaternary ammonium salts such as [(C$_{14}$H$_{32}$N$_2$)(OH)$_2$]$_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired FCAPOs of the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ions; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2.2.2) octane ion; di-n-butylamine, neopentylamine; di-n-pentylamine, isopropylamine; t-butylamine; ethylenediamine; pyrrolidine; and 2-imidazolidone. Not every templating agent will direct the formation of every species of FCAPO, i.e., a single templating agent can, with proper manipulation of the reaction conditions, direct the formation of several FCAPO compositions, and a given FCAPO composition can be produced using several different templating agents.

The preferred phosphorus source for the present process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently, serve as reactive sources of phosphorus, but these compounds may function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudo-boehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The elements arsenic, beryllium, boron, chromium, gallium, germanium, lithium and vanadium can be introduced into the reaction system in any form which permits the formation in situ of reactive form of the element, i.e., reactive to form the framework tetrahedral unit "$MO_2^n$" of the element. Compounds which may be employed include: oxides; alkoxides; hydroxides; halides; chlorides; iodides; sulfates; bromides; organic salts such as carboxylates (e.g., acetates); nitrates; and the like.

While not essential to the synthesis of FCAPO compositions, stirring or other moderate agitation of the reaction mixture and/or seeding the reaction mixture with seed crystals of either the FCAPO species to be produced or a topologically similar aluminophosphate, aluminosilicate or molecular sieve composition, facilitates the crystallization procedure.

After crystallization the FCAPO product may be isolated and advantageously washed with water and dried in air. The as-synthesized FCAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular FCAPO species. As a general rule the templating agent, and hence the occluded organic species, is too large to move freely through the pore system of the FCAPO product and must be removed by calcining the FCAPO at temperatures of 200° C. to 700° C. to thermally degrade the organic species. In a few instances the pores of the FCAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the FCAPO phase wherein the organic moiety occupying the intracrystalline pore system as a result of the hydrothermal crystallization process has been reduced by post-synthesis treatment such that the value of "m" in the composition formula $$mR:(M_xAl_yP_z)O_2$$

has a value of less than 0.02. The other symbols of the formula are as defined hereinabove. In those preparations in which an aluminum alkoxide is employed as the source of "M", aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized FCAPO material.

Since the present FCAPO compositions are formed from $MO_2^n$, $AlO_2$, and $PO_2$ tetrahedral units which, respectively, have a net charge of "n", $-1$ and $+1$, where "n" is $-3$, $-2$, $-1$, 0 or $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of "M" present in the reaction mixture, or an organic cation derived from the templating agent. Similarly a $MO_2^n$ tetrahedron can be balanced electrically by association with $PO_2^+$ or $AlO_2^-$ tetrahedra, a cation of "M" present in the reaction mixture, a simple cation unless such as an alkali metal cation, a proton ($H^+$), organic cations derived from the templating agent, or other divalent or polyvalent metal anions or cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, D.C. (1971)].

The FCAPO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of FCAPO compositions is ordinarily possible only after the organic moiety derived from the template, present as a result of synthesis, has been removed from the pore system. Dehydration to remove water present in the as-synthesized FCAPO compositions can usually be accomplished, to some degree at least, in the usual manner without removal of the organic moiety, but the absence of the organic species greatly facilitates adsorption and desorption procedures. As illustrated hereinafter, the FCAPO materials have various degrees of hydrothermal and thermal stability, some being quite remarkable in this regard, and function well as molecular sieve adsorbents and hydrocarbon conversion catalysts or catalyst bases.

In preparing the FCAPO compositions it is preferred to use a stainless steel reaction vessel utilized lined with an inert plastic material, polytetrafluoroethylene, to avoid contamination of the reaction mixture. In general, the final reaction mixture from which each FCAPO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

X-ray patterns of reaction products are obtained by X-ray analysis using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant, Interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively the X-ray analysis may be carried out using copper K-alpha radiation with Siemens Type K-805 X-ray sources and Siemens D-500 X-ray powder diffractometers, available from Siemens Corporation, Cherry Hill, N.J.

As will be understood by those skilled in the art the determinatiobn of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs. s, m, w and vw which represent very strong, strong, medium, weak and very weak respectively.

In certain instances, the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through V, wherein said x-ray patterns are for both the as-synthesized and calcined forms unless otherwise noted:

TABLE A (FCAPO-5)

| $2\theta$ | d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B (FCAPO-11)

| $2\theta$ | d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

TABLE C (FCAPO-14)

| $2\theta$ | d(Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D (FCAPO-16)

| $2\theta$ | d(Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E (FCAPO-17)

| $2\theta$ | d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F (FCAPO-18)

| $2\theta$ | d(Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |

TABLE F-continued

(FCAPO-18)

| 2θ | d(Å) | Relative Intensity |
|---|---|---|
| 20.95–21.05 | 4.24–4.22 | m |
| 31.8–32.5 | 2.814–2.755 | m |

TABLE G

(FCAPO-20)

| 2θ | d(Å) | Relative Intensity |
|---|---|---|
| 13.7–14.25 | 6.46–6.22 | m–vs |
| 19.55–20.0 | 4.54–4.44 | w–s |
| 24.05–24.5 | 3.70–3.63 | m–vs |
| 34.3–35.0 | 2.614–2.564 | vw–w |
| 42.5–43.0 | 2.127–2.103 | vw–w |

TABLE H

(FCAPO-31)

| 2θ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

(FCAPO-33)

| 2θ | d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

(FCAPO-33)

| 2θ | d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

(FCAPO-34)

| 2θ | d(Å) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

(FCAPO-35)

| 2θ | d(Å) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

(FCAPO-36)

| 2θ | d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE O

(FCAPO-37)

| 2θ | d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

(FCAPO-39)

| 2θ | d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

(FCAPO-40)

| 2θ | d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

(FCAPO-41)

| 2θ | d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

(FCAPO-42)

| 2θ | d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

(FCAPO-44)

| 2θ | d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |

TABLE T-continued

| 2θ | (FCAPO-44) d(Å) | Relative Intensity |
|---|---|---|
| 20.6–20.85 | 4.31–4.26 | s–vs |
| 24.3–24.4 | 3.66–3.65 | w–vs |
| 30.7–30.95 | 2.912–2.889 | w–s |

TABLE U

| 2θ | (FCAPO-46) d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| 2θ | (FCAPO-47) d(Å) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

The following examples are provided to further illustrate the invention and are not intended to be limiting thereof:

EXAMPLE 1

(Preparation of AsGaAPO-5)

(a) AsGaAPO-5 is prepared from a reaction mixture having a composition, expressed in terms of the molar oxide ratios of the components of the reaction mixture, of:

1.0–2.0TPA:0.05–0.2(M)$_2$O$_q$:0.5–1.0Al$_2$O$_3$:0.5–1.0-P$_2$O$_5$:40–100H$_2$O where "TPA" denotes tripropylamine and "q" denotes the oxidation state(s) of "M" (arsenic and gallium).

The reaction mixture is digested by placing the reaction mixture in a sealed stainless steel pressure vessel and heating it at an effective temperature and for an effective time to produce the AsGaAPO-5 product. Solids are recovered by filtration, washed with water and dried in air at room temperature.

The AsGaAPO-5 product's chemical analysis shows the AsGaAPO-5 product contains arsenic, gallium, aluminum and phosphorus in amounts within the pentagonal compositional area defined by points A, B, C, D and E of FIG. 1.

The x-ray powder diffraction pattern of a AsGaAPO-5 product is characterized by the following data:

| 2θ | d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

(b) The x-ray powder diffraction pattern for a calcined AsGaAPO-5 is also characterized by the pattern of part (a).

(c) When the calcined AsGaAPO-5 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp. °C. | Wt. % Adsorbed* |
|---|---|---|---|---|
| O$_2$ | 3.46 | 100 | −183 | 7 |
| O$_2$ | 3.46 | 750 | −183 | 10 |
| Neopentane | 6.2 | 700 | 24 | 4 |
| H$_2$O | 2.65 | 4.3 | 24 | 4 |
| H$_2$O | 2.65 | 20.0 | 24 | 12 |

*typical amount adsorbed

The pore diameter of AsGaAPO-5 is greater than 6.2 Å.

EXAMPLE 2

(Preparation of BeGeAPO-11)

(a) BeGeAPO-11 is prepared from a reaction mixture having a composition, expressed in terms of the molar oxide ratios of the components of the reaction mixture, of:

1.0–2.0DPA:0.05–0.2
(M)$_2$O$_q$:0.5–1.0Al$_2$O$_3$:0.5–1.0P$_2$O$_5$:40–100H$_2$O where "DPA" denotes di-n-propylamine and "q" denotes the oxidation state(s) of "M" (beryllium and germanium).

The reaction mixture is digested by placing the reaction mixture in a sealed stainless steel pressure vessel and heating it at an effective temperature and for an effective time to produce the BeGeAPO-11 product. Solids are then recovered by filtration, washed with water and dried in air at room temperature.

The BeGeAPO-11 product's chemical analysis shows the BeGeAPO-11 product contains beryllium, germanium, aluminum and phosphorus in amounts within the pentagonal compositional area defined by points A, B, C, D and E of FIG. 1.

The x-ray powder diffraction pattern of a BeGeAPO-11 product is characterized by the following data:

| 2θ | d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

(b) The x-ray powder diffraction pattern for a calcined BeGeAPO-11 is also characterized by the X-ray pattern of part (a).

(c) When the calcined BeGeAPO-11 of part (b) is utilized in absorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp. °C. | Wt. % Adsorbed* |
|---|---|---|---|---|
| O$_2$ | 3.46 | 100 | −183 | 5 |
| O$_2$ | 3.46 | 750 | −183 | 6 |

| Adsorbate | Kinetic Diameter(Å) | Pressure (Torr) | Temp. °C | Wt. % Adsorbed* |
|---|---|---|---|---|
| Cyclohexane | 6.0 | 90 | 24 | 4 |
| $H_2O$ | 2.65 | 4.3 | 24 | 6 |
| $H_2O$ | 2.65 | 20 | 24 | 8 |

*typical amount adsorbed

The pore diameter of BeGeAPO-11 is about 6 Å.

EXAMPLE 3

(Preparation of CrGaAPO-17)

(a) CrGaAPO-17 is prepared from a reaction mixture having a composition, expressed in terms of the molar oxide ratios of the components of the reaction mixture, of:

1.0–2.0QN:0.05–0.2(M)$_2$O$_q$:0.5–1.0Al$_2$O$_3$:0.5–1.0-P$_2$O$_5$:40–100H$_2$O where "QN" denotes quinuclidine and "q" denotes the oxidation state(s) of "M" (chromium and gallium).

The reaction mixture is digested by placing the reaction mixture in a sealed stainless steel pressure vessel and heating it at an effective temperature and for an effective time to produce the CrGaAPO-17 product. Solids are then recovered by filtration, washed with water and dried in air at room temperature.

The CrGaAPO-17 product's chemical analysis shows the CrGaAPO-17 product contains chromium, gallium, aluminum and phosphorus in amounts within the pentagonal compositional area defined by points A, B, C, D and E of FIG. 1.

The x-ray powder diffraction pattern of a CrGaAPO-17 product is characterized by the following data:

| 2θ | d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

(b) The x-ray powder diffraction pattern for a calcined CrGaAPO-17 is also characterized by the X-ray pattern of part (a).

(c) When the calcined CrGaAPO-17 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp. °C | Wt. % Adsorbed* |
|---|---|---|---|---|
| $O_2$ | 3.46 | 100 | −183 | 10 |
| $O_2$ | 3.46 | 750 | −183 | 12 |
| n-butane | 4.3 | 100 | 24 | 4 |
| $H_2O$ | 2.65 | 4.3 | 24 | 13 |
| $H_2O$ | 2.65 | 20 | 24 | 14 |

*typical amount adsorbed

The pore diameter of CrGaAPO-17 is about 4.3 Å.

EXAMPLE 4

(Preparation of AsBeAPO-31)

(a) AsBeAPO-31 is prepared from a reaction mixture having a composition, expressed in terms of the molar oxide ratios of the components of the reaction mixture, of:

1.0–2.0DPA:0.05–0.2(M)$_2$O$_q$:0.5–1.0Al$_2$O$_3$:0.5–1.0-P$_2$O$_4$:40–100H$_2$O where "DPA" denotes di-n-propylamine and "q" denotes the oxidation state of "M" (arsenic and beryllium).

The reaction mixture is seeded with crystals of AlPO$_4$-31 (U.S. Pat. No. 4,310,440) and digested by placing the reaction mixture in a sealed stainless steel pressure vessel and heating it at an effective temperature and for an effective time to produce the AsBeAPO-31 product. Solids are then recovered by filtration, washed with water and dried in air at room temperature.

The AsBeAPO-31 product's chemical analysis shows the AsBeAPO-31 product contains arsenic, beryllium, aluminum and phosphorus in amounts within the pentagonal compositional area defined by points A, B, C, D and E of FIG. 1.

The x-ray powder diffraction pattern of a AsBeAPO-31 product is characterized by the following data:

| 2θ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

(b) The x-ray powder diffraction pattern for a calcined AsBeAPO-31 is also characterized by the X-ray pattern of part (a).

(c) When the calcined AsBeAPO-31 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp. °C | Wt. % Adsorbed* |
|---|---|---|---|---|
| $O_2$ | 3.46 | 100 | −183 | 4 |
| $O_2$ | 3.46 | 750 | −183 | 6 |
| Cyclohexane | 6.0 | 90 | 24 | 3 |
| Neopentane | 6.2 | 700 | 24 | 3 |
| $H_2O$ | 2.65 | 4.3 | 24 | 3 |
| $H_2O$ | 2.65 | 20 | 24 | 10 |

*typical amount adsorbed

The pore diameter of AsBeAPO-31 is greater than about 6.2 Å.

EXAMPLE 5

(Preparation of AsVBeAPO-34)

(a) AsVBeaPO-34 is prepared from a reaction mixture having a composition, expressed in terms of the molar oxide ratios of the components of the reaction mixture, of:

1.0–2.0TEAOH:0.05–0.2(M)$_2$O$_q$:0.5–1.0Al$_2$O$_3$:0-.5–1.0$_2$O$_5$:40–100H$_2$O where "TEAOH" denotes tetraethylammonium hydroxide and "q" denotes the oxidation state of "M" (arsenic, vanadium, and beryllium).

The reaction mixture is digested by placing the reaction mixture in a sealed stainless steel pressure vessel and heating it at an effective temperature and for an effective time to produce the AsVBeAPO-34 product. The solids are recovered by filtration, washed with water and dried in air at room temperature.

The AsVBeAPO-34 product's chemical analysis shows the AsVBeAPO-34 product contains arsenic, vanadium, beryllium, aluminum and phosphorus in amounts within the pentagonal compositional area defined by points A, B, C, D and E of FIG. 1.

The x-ray powder diffraction pattern of a AsVBeAPO-34 product is characterized by the following data:

| $2\theta$ | $d(\text{Å})$ | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

(b) The x-tay powder diffraction pattern for a calcined AsVBeAPO-34 is pattern of part (a).

(c) When the calcined AsVBeAPO-34 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp. °C. | Wt. % Adsorbed* |
|---|---|---|---|---|
| $O_2$ | 3.46 | 100 | −183 | 13 |
| $O_2$ | 3.46 | 750 | −183 | 18 |
| n-hexane | 4.3 | 100 | 24 | 6 |
| $H_2O$ | 2.65 | 4.3 | 24 | 15 |
| $H_2O$ | 2.65 | 20 | 24 | 21 |

*typical amount adsorbed

The pore diameter of AsVBeAPO-34 is about 4.3 Å.

EXAMPLE 6

(Preparation of GeBAPO-44)

(a) GeBAPO-44 is prepared from a reaction mixture having a composition, expressed in terms of the molar oxide ratios of the components of the reaction mixture, of:

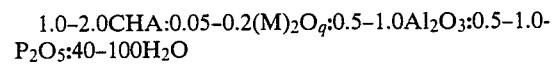

where "CHA" denotes cyclohexylamine and "q" denotes the oxidation state of "M" (boron and germanium).

The reaction mixture is digested by placing the reaction mixture in a sealed stainless steel pressure vessel and heating it at an effective temperature and for an effective time to produce GeBAPO-44 product. Solids are then recovered by filtration, washed with water and dried in the air at room temperature.

The GeBAPO-44 product's chemical analysis shows the GeBAPO-44 product contains boron, germanium, aluminum and phosphorus in amounts within the pentagonal compositional area defined by points A, B, C, D and E of FIG. 1.

The x-ray powder diffraction pattern of a GeBAPO-44 product is characterized by the following data:

| $2\theta$ | $d(\text{Å})$ | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

(b) When the calcined GeBAPO-44 is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp. °C. | Wt. % Adsorbed* |
|---|---|---|---|---|
| $O_2$ | 3.46 | 100 | −183 | 13 |
| $O_2$ | 3.46 | 750 | −183 | 16 |
| n-hexane | 4.3 | 100 | 24 | 2 |
| $H_2O$ | 2.65 | 4.3 | 24 | 15 |
| $H_2O$ | 2.65 | 20 | 24 | 17 |

*typical amount adsorbed

The pore diameter of GeBAPO-44 is about 4.3 Å.

PROCESS APPLICATIONS

The FCAPO compositions of the present invention are, in general, hydrophilic and adsorb water preferentially over common hydrocarbon molecules such as paraffins, olefins and aromatic species, e.g., benzene, xylenes and cumene. Thus, the present FCAPO compositions as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These FCAPOs are therefore suitably employed in the drying of reformer hydrogen streams and in the drying of oxygen, nitrogen or air prior to liquifaction.

The present FCAPO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4 Å are preferred for catalytic applications.

Among the hydrocarbon conversion reactions catalyzed by FCAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using FCAPO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The FCAPO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (hydrogen/hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$-$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present FCAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with FCAPO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the FCAPO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°-1000° F. are employed at moderate hydrogen pressures of about 300-1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hyrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°-900° F., while paraffins, naphthenes and alkyl aromatics are isomerized at temperatures of 700°-1000° F. Particularly desirable isomerization reactions contemplated herein include the conversion of n-heptane and/or n-octane to isoheptanes, iso-octanes, butane to iso-butane, methylcyclopentane to cyclohexane, meta-xylene and-/or ortho-xylene to paraxylene, 1-butene to 2-butene and/or isobutene, n-hexene to isohexene, cyclohexene to methylcyclopentene etc. The preferred form of the catalyst is a combination of the FCAPO with polyvalent metal compounds (such as sulfides) of metals of Group II-A, Group II-B and rare earth metals. For alkylation and dealkylation processes the FCAPO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylation agents are olefins such as ethylene and propylene.

We claim:

1. Crystalline molecular sieves having three-dimensional microporous framework structures of $MO_2$, $AlO_2$ and $PO_2$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least two elements, $M_1$ and $M_2$, selected from the group consisting of arsenic, beryllium, boron, chromium, gallium, germanium, lithium and vanadium; and "x", "y" and "z" represent the mole fractions of M ($=M_1+M_2$ etc.), aluminum and phosphorus, respectively, present as tetrahedral oxides, said mole fractions being such that they are within the pentagonal compositional area defined by points A, B, C, D and E of FIG. 1 and each mole fraction for $M_1$, $M_2$, aluminum and phosphorus has a value of at least 0.01, said crystalline molecular sieves having a characteristic X-ray powder diffraction pattern which contains at least the d-spacings set forth in one of Tables A to H and J to V herein.

2. Molecular sieves according to claim 1 wherein the mole fractions of "M", aluminum and phosphorus present as tetrahedral oxides are within the hexagonal compositional area defined by points a, b, c, d, e and f of FIG. 2.

3. The crystalline molecular sieves of claim 1 or 2 having a characteristic X-ray powder diffraction pattern which contains at least the d-spacings set forth in Table A.

4. The crystalline molecular sieves of claim 1 or 2 having a characteristic X-ray powder diffraction pattern which contains at least the d-spacings set forth in Table B.

5. The crystalline molecular sieves of claim 1 or 2 having a characteristic X-ray powder diffraction pattern which contains at least the d-spacings set forth in Table C.

6. The crystalline molecular sieves of claim 1 or 2 having a characteristic X-ray powder diffraction pattern which contains at least the d-spacings set forth in Table D.

7. The crystalline molecular sieves of claim 1 or 2 having a characteristic X-ray powder diffraction pattern which contains at least the d-spacings set forth in Table E.

8. The crystalline molecular sieves of claim 1 or 2 having a characteristic X-ray powder diffraction pattern which contains at least the d-spacings set forth in Table F.

9. The crystalline molecular sieves of claim 1 or 2 having a characteristic X-ray powder diffraction pattern which contains at least the d-spacings set forth in Table G.

10. The crystalline molecular sieves of claims 1 or 2 having a characteristic x-ray powder diffraction pattern which contains at least the d-spacings set forth in Table H.

11. The crystalline molecular sieves of claims 1 or 2 having a characteristic x-ray powder diffraction pattern which contains at least the d-spacings set forth in Table J.

12. The crystalline molecular sieves of claims 1 or 2 having a characteristic x-ray powder diffraction pattern which contains at least the d-spacings set forth in Table K.

13. The crystalline molecular sieves of claims 1 or 2 having a characteristic x-ray powder diffractions pattern which contains at least the d-spacing set forth in Table L.

14. The crystalline molecular sieves of claims 1 or 2 having a characteristic x-ray powder diffraction pattern which contains at least the d-spacings set forth in Table M.

15. The crystalline molecular sieves of claims 1 or 2 having a characteristic x-ray powder diffraction pattern which contains at least the d-spacings set forth in Table N.

16. The crystalline molecular sieves of claims 1 or 2 having a characteristic x-ray powder diffraction pattern which contains at least the d-spacings set forth in Table O.

17. The crystalline molecular sieves of claims 1 or 2 having a characteristic x-ray powder diffraction pattern which contains at least the d-spacings set forth in Table P.

18. The crystalline molecular sieves of claims 1 or 2 having a characteristic x-ray powder diffraction pattern which contains at least the d-spacings set forth in Table Q.

19. The crystalline molecular sieves of claims 1 or 2 having a characteristic x-ray powder diffraction pattern which contains at least the d-spacings set forth in Table R.

20. The crystalline molecular sieves of claims 1 or 2 having a characteristic x-ray powder diffraction pattern which contains at least the d-spacings set forth in Table S.

21. The crystalline molecular sieves of claims 1 or 2 having a characteristic x-ray powder diffraction pattern which contains at least the d-spacings set forth in Table T.

22. The crystalline molecular sieves of claims 1 or 2 having a characteristic x-ray powder diffraction pattern which contains at least the d-spacings set forth in Table U.

23. The crystalline molecular sieves of claims 1 or 2 having a characteristic x-ray powder diffraction pattern which contains at least the d-spacings set forth in Table V.

24. The molecular sieves according to claim 1 wherein "M" is arsenic and germanium.

25. Molecular sieves according to claim 1 wherein "M" is beryllium and germanium.

26. Molecular sieves according to claim 1 wherein "M" is chromium and gallium.

27. The molecular sieves according to claim 1 wherein "M" is arsenic and beryllium.

28. The molecular sieves according to claim 1 wherein "M" is arsenic, vanadium and beryllium.

29. The molecular sieves of claim 1 wherein "M" is germanium and boron.

30. The molecular sieves of claim 1 wherein "M" is at least two elements selected from the group consisting of boron, chromium, vanadium, arsenic, germanium and gallium.

31. Process for preparing the crystalline molecular sieves of claim 1 which comprises providing a reaction mixture composition expressed in terms of molar oxide ratios as follows:

$$aR:(M_xAl_yP_z)O_2:bH_2O$$

wherein "R" is an organic templating agent: "a" is the amount of "R" and is an effective amount greater than zero: "b" has a value of from zero to about 500, "M" represents at least two elements capable of forming framework tetrahedral oxides and selected from the group consisting of arsenic, beryllium, boron, chromium, gallium, germanium, lithium and vanadium; "x", "y" and "z" represent the mole fractions, respectively, of "M", aluminum and phosphorus in the $(M_xAl_yP_z)O_2$ constituent, and each has a value of at least 0.01, whereby the molecular sieves of claim 1 are prepared.

32. The process of claim 31 where "x", "y" and "z" are within the hexagonal compositional area defined by points F, G, H, I, J and K which is FIG. 3 of the drawings.

33. Process according to claim 31 wherein "a" is an effective amount from greater than zero to about 6.

34. Process according to claim 31 wherein the source of phosphorus in the reaction mixture is orthophosphoric acid.

35. Process according to claim 31 wherein the source of phosphorus in the reaction mixture is orthophosphoric acid and the source of aluminum is at least one compound selected from the group consisting of pseudoboehmite and aluminum alkoxide.

36. Process according to claim 35 wherein the aluminum alkoxide is aluminum isopropoxide.

37. Process according to claim 35 wherein the source of "M" is selected from the group consisting of chlorides, bromide, iodides, sulfates, nitrates, acetates and formates.

38. Process according to claim 31 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

39. Process according to claim 31 wherein the organic templating agent is an amine.

40. Process according to claim 31 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-diethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $[(C_{14}H_{32}N_2)(OH)_2]_x$ wherein x is a value of at least 2.

41. Molecular sieve prepared by calcining the composition of claim 1 or claim 2 at a temperature sufficiently high to remove at least some of the organic templating agent present in the intracrystalline pore system.

42. Crystalline molecular sieves having three-dimensional microporous framework structures of $MO_2$, $AlO_2$ and $PO_2$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least two elements, $M_1$ and $M_2$, selected from the group consisting of arsenic, beryllium, boron, chromium, gallium, germanium, lithium and vanadium; and "x", "y" and "z" represent the mole fractions of M ($=M_1+M_2$ etc.), aluminum and phosphorus, respectively, present as tetrahedral oxides, said mole fractions being such that they are within the pentagonal compositional area defined by points A, B, C, D and E of FIG. 1 and each mole fraction for $M_1$, $M_2$, aluminum and phosphorus has a value of at least 0.01.

43. Crystalline molecular sieves according to claim 42 wherein the mole fractions of "M", aluminum and phosphorus present as tetrahedral oxides are within the tetragonal compositional area defined by points a, b, c, d, e and f of FIG. 2.

44. Process for preparing crystalline molecular sieves of claim 42 having three-dimensional framework structures wherein the process comprises providing at an effective temperature and for an effective time a reaction mixture composition expressed in terms of molar oxide ratios as follows:

$$aR:(M_xAl_yP_z)O_2:bH_2O$$

wherein "R" is an organic templating agent; "a" is an effective amount of "R" greater than zero; "b" has a value of from zero to about 500; "M" represents at least two elements capable of forming tetrahedral oxides and selected from the group consisting of arsenic, beryllium, boron, chromium, gallium, germanium, lithium and vanadium; "x", "y" and "z" represent the mole fractions, respectively, of "M", aluminum and phosphorus in the $(M_xAl_yP_z)O_2$ constituent, and each has a value of at least 0.01, whereby molecular sieves according to claim 64 are prepared.

45. Molecular sieve prepared by calcining the compositions of claim 42 or 43 at a temperature sufficiently high to remove at least some of the organic templating agent present in the intracrystalline pore system.

* * * * *